(12) United States Patent
Takano et al.

(10) Patent No.: US 11,186,537 B2
(45) Date of Patent: Nov. 30, 2021

(54) METHOD FOR PRODUCING COMPOUND, COMPOUND, EPOXY CURING AGENT, AND METHOD FOR PRODUCING AMINE COMPOSITION

(71) Applicant: MITSUBISHI GAS CHEMICAL COMPANY, INC., Tokyo (JP)

(72) Inventors: Yoichi Takano, Tokyo (JP); Kazuyoshi Uera, Tokyo (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 17/057,463

(22) PCT Filed: May 28, 2019

(86) PCT No.: PCT/JP2019/021020
§ 371 (c)(1),
(2) Date: Nov. 20, 2020

(87) PCT Pub. No.: WO2019/230692
PCT Pub. Date: Dec. 5, 2019

(65) Prior Publication Data
US 2021/0198181 A1    Jul. 1, 2021

(30) Foreign Application Priority Data

May 31, 2018  (JP) .............................. JP2018-104381
Feb. 26, 2019  (JP) .............................. JP2019-032381
Feb. 26, 2019  (JP) .............................. JP2019-032384

(51) Int. Cl.
*C07C 209/68*    (2006.01)
*C07C 211/27*    (2006.01)
*C08G 59/50*     (2006.01)

(52) U.S. Cl.
CPC .......... *C07C 209/68* (2013.01); *C07C 211/27* (2013.01); *C08G 59/5033* (2013.01)

(58) Field of Classification Search
CPC ............................ C07C 209/68; C07C 211/27
See application file for complete search history.

(56) References Cited

U.S. PATENT DOCUMENTS

| | | | | |
|---|---|---|---|---|
| 2,762,845 A | * | 9/1956 | Ebersberger .......... | C07C 209/68 564/409 |
| 3,652,685 A | * | 3/1972 | Geddes, Jr. ........... | C07C 209/68 568/756 |
| 8,058,384 B2 | * | 11/2011 | Kato ...................... | C08G 64/14 528/196 |
| 2005/0038298 A1 | | 2/2005 | Echigo et al. | |
| 2005/0137424 A1 | | 6/2005 | Kuwahara et al. | |
| 2013/0303805 A1 | | 11/2013 | Kuwahara et al. | |
| 2019/0112416 A1 | | 4/2019 | Sato et al. | |

FOREIGN PATENT DOCUMENTS

| | | |
|---|---|---|
| JP | 2005-89455 A | 4/2005 |
| JP | 2005-179204 A | 7/2005 |
| JP | 2011-88863 A | 5/2011 |
| JP | 5486537 B2 | 5/2014 |
| JP | 2019-64978 A | 4/2019 |
| WO | 2012/105303 A1 | 8/2012 |
| WO | 2017/175740 A1 | 10/2017 |
| WO | 2017/175741 A1 | 10/2017 |

OTHER PUBLICATIONS

J. Dalmolen et al., 11 Chemistry—A European Journal, 5619-5624 (2005) (Year: 2005).*
CAS Abstract RN 1824379-38-5 (2015) (Year: 2015).*
CAS Registry Numbers (2016) (Year: 2016).*
Dalmolen, J. et al., "The Dutch Resolution Variant of the Classical Resolution of Racemates by Formation of Diastereomeric Salts: Family Behaviour in Nucleation Inhibition" Chem. Eur. J., 2005, pp. 5619-5624.
RN 2165500-08-1 Registry, Registry (SIN), Dec. 27, 2017.
RN 1824379-38-5 Registry, Registry (SIN), Dec. 7, 2015.
International Search Report issued in International Patent Application No. PCT/JP2019/021020, dated Aug. 13, 2019 and English Translation thereof.

(Continued)

*Primary Examiner* — Alexander R Pagano
(74) *Attorney, Agent, or Firm* — Greenblum & Bernstein, P.L.C.

(57) ABSTRACT

Provided are: a method for producing a compound that excels in storage stability and handleability; the compound; and an epoxy curing agent containing the compound. The method for producing a compound represented by Formula (1-1) includes subjecting the compound represented by Formula (5-1) to an addition reaction to add ethylene and/or propylene in the presence of a base. In Formula (5-1), $R^X$ to $R^Z$ each independently represent a hydrogen atom, an ethyl group, an n-propyl group, or an isopropyl group, and n is an integer of from 1 to 3. In Formula (1-1), $R^A$ to $R^D$ each independently represent a hydrogen atom, an ethyl group, an n-propyl group, or an isopropyl group, and n is an integer of from 1 to 3.

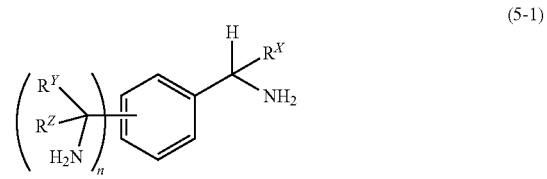

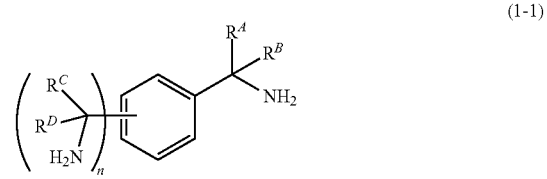

22 Claims, No Drawings

(56) References Cited

OTHER PUBLICATIONS

International Preliminary Report on Patentability issued in International Patent Application No. PCT/JP2019/021020, dated Dec. 1, 2020 and English Translation thereof.
Written Opinion of The International Searching Authority issued in International Patent Application No. PCT/JP2019/021020, dated Aug. 13, 2019 and English Translation thereof.

* cited by examiner

METHOD FOR PRODUCING COMPOUND, COMPOUND, EPOXY CURING AGENT, AND METHOD FOR PRODUCING AMINE COMPOSITION

TECHNICAL FIELD

The present invention relates to a method for producing a compound, the compound, an epoxy curing agent, and a method for producing an amine composition.

BACKGROUND ART

Amine compounds are useful as raw materials and intermediates for compounds to be used as pharmaceuticals, agricultural chemicals, and the like, and therefore a wide variety of amine compounds are known.

As one type of amine compound, an aromatic diamine compound, which is a compound having two or more aminomethyl groups in an aromatic ring such as benzene, is known. Examples of the aromatic diamine compound include meta-xylylenediamine and the like.

The amine compound can also be used as an epoxy curing agent. For example, Patent Documents 1 and 2 disclose that polyamine compounds having a specific structure can be used as epoxy resin curing agents.

Patent Document 1 also discloses a method for producing the following polyamine compound, the method having a step of subjecting xylylenediamine and a conjugated diene to an addition reaction in the presence of a basic catalyst.

[Chem. 1]

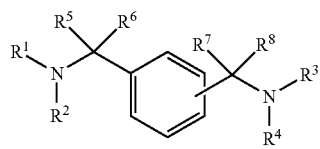

(I)

In Formula (I), $R^1$ to $R^4$ are each independently a hydrogen atom, a chain-shaped unsaturated aliphatic hydrocarbon group having from 2 to 10 carbons, or a cyclic unsaturated aliphatic hydrocarbon group having a ring member with from κ to 10 carbons. However, at least one of $R^1$ to $R^4$ is a hydrogen atom. $R^5$ to $R^8$ are each independently a hydrogen atom, a chain-shaped unsaturated aliphatic hydrocarbon group having from 2 to 10 carbons, or a cyclic unsaturated aliphatic hydrocarbon group having a ring member with from 5 to 10 carbons. However, not all of $R^1$ to $R^8$ are hydrogen atoms, and at least one of $R^1$ to $R^8$ is a chain-shaped unsaturated aliphatic hydrocarbon group having from 2 to 10 carbons or a cyclic unsaturated aliphatic hydrocarbon group having a ring member with from 5 to 10 carbons.

CITATION LIST

Patent Documents

Patent Document 1: WO 2017/175741
Patent Document 2: JP 5486537 B

SUMMARY OF INVENTION

Technical Problem

As described above, amine compounds can be used as raw materials and intermediates for pharmaceuticals, agricultural chemicals, and the like, and amine compounds of various structures are required to diversify the structure of compounds that are used in these applications in order to create new pharmaceuticals and agricultural chemicals.

Furthermore, amine compounds such as meta-xylylenediamine are highly reactive, and react with carbon dioxide or the like in the air during storage, resulting in the formation of carbonates. When carbonates are formed, careful attention is required during handling because such carbonates lead to a change in the raw material charging ratio due to a decrease in purity, and to a deterioration in the physical properties of the cured product when used as an epoxy resin curing agent (storage stability).

Furthermore, because the melting point of meta-xylylenediamine is 14° C., meta-xylylenediamine is easily crystallized when handled at low temperatures, and thus another problem is difficult handling (handleability).

Storage stability can be improved by using an inert gas atmosphere as the storage environment or by preparing and storing a mixture with a compound that does not react with carbon dioxide. However, if the storage environment is an inert gas atmosphere, operations become complicated. Furthermore, for a case in which a mixture is formed with a compound that does not react with carbon dioxide and the mixture is stored, when an amine compound is used as a substrate for an organic reaction, the compound that does not react with carbon dioxide may inhibit the reaction or cause an increase in side reactants. Therefore, it is necessary to configure such that the amine compound can be stored in an air atmosphere in a pure substance state.

The handleability can be improved by adding additives such as a melting point adjusting agent to the amine compound. However, in cases in where an amine compound is used as a substrate for an organic reaction, the addition of these additives may inhibit the reaction or increase the side reactants, and therefore it is necessary to improve the handleability without the addition of additives.

Also, improving storage stability and handleability is also beneficial when using an amine compound as an epoxy curing agent.

In light of the foregoing, an object of the present invention is to provide a compound excelling in storage stability and handleability, a method for producing the compound, and an epoxy curing agent containing the compound.

Solution to Problem

As a result of diligent research, the present inventors discovered that a predetermined compound excels in storage stability and handleability, and thus completed the present invention.

That is, the present invention is as follows.

<1> A method for producing a compound represented by Formula (1-1), the method including subjecting a compound represented by Formula (5-1) to an addition reaction to add ethylene and/or propylene in the presence of a base:

[Chem. 2]

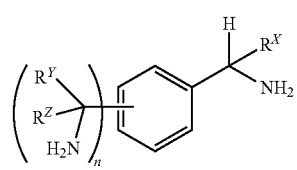

(5-1)

where in Formula (5-1), $R^X$ to $R^Z$ each independently represent a hydrogen atom, an ethyl group, an n-propyl group, or an isopropyl group, and n is an integer of from 1 to 3;

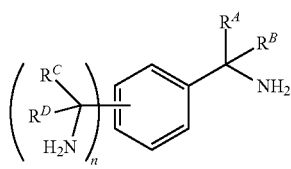

(1-1)

where in Formula (1-1), $R^A$ to $R^D$ each independently represent a hydrogen atom, an ethyl group, an n-propyl group, or an isopropyl group, and n is an integer of from 1 to 3, wherein at least two of $R^A$ to $R^D$ are independently an ethyl group, an n-propyl group, or an isopropyl group, and Formula (1-1) excludes: a case where n is 1, a —C($R^C$)($R^D$)(NH$_2$) group is at para position and at meta position, and either $R^A$ or $R^B$, and either $R^C$ or $R^D$ are each an n-propyl group, and the remaining two of $R^A$ to $R^D$ are hydrogen atoms; and a case where n is 1, a —C($R^C$)($R^D$)(NH$_2$) group is at ortho position, either $R^A$ or $R^B$, and either $R^C$ or $R^D$ are each an ethyl group, and the remaining two of $R^A$ to $R^D$ are hydrogen atoms.

<2> A method for producing a compound represented by Formula (1-2), the method including filling a compound represented by Formula (5-2) with ethylene and subjecting to alkylation in the presence of a base, wherein a temperature of a reaction solution at the time of ethylene filling is from 0 to 10° C., and a filling pressure of the ethylene is from 1.5 to 2.3 MPa:

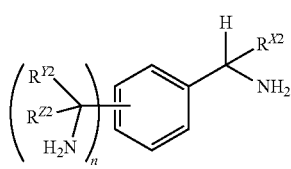

(5-2)

where in Formula (5-2), $R^{X2}$ to $R^{Z2}$ each independently represent a hydrogen atom or an ethyl group, and n is an integer of from 1 to 3;

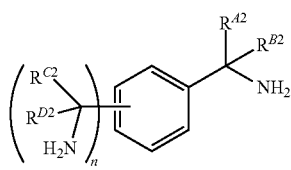

(1-2)

where in Formula (1-2), $R^{A2}$ to $R^{D2}$ each independently represent a hydrogen atom or an ethyl group, and n is an integer of from 1 to 3, wherein at least two of $R^{A2}$ to $R^{D2}$ are ethyl groups.

<3> The compound production method according to <1> or <2>, wherein the base is a base composition containing: at least one alkali metal-containing compounds (A) selected from the group consisting of rubidium carbonate, rubidium hydroxide, cesium carbonate, and cesium hydroxide; and a metallic sodium (B).

<4> The compound production method according to any one of <1> to <3>, wherein the method includes dividing the base into two or more portions and introducing into a reaction system.

<5> The compound production method according to any one of <1> to <4>, wherein n in Formula (5-1) and/or Formula (5-2) is 1.

<6> The compound production method according to any one of <1> to <4>, wherein the compound represented by Formula (5-1) and/or the compound represented by Formula (5-2) includes at least one compound selected from the group consisting of benzylamine, α-methyl benzenemethanamine, α-ethyl benzenemethanamine, o-xylylenediamine, m-xylylenediamine, p-xylylenediamine, 1,2,3-benzene trimethanamine, 1,2,4-benzene trimethanamine and 1,2,4,5-benzene tetramethanamine.

<7> The compound production method according to any one of <1> to <4>, wherein the compound represented by Formula (5-1) and/or the compound represented by Formula (5-2) includes m-xylylenediamine.

<8> The compound production method according to any one of <1> to <7>, wherein the compound represented by Formula (1-1) is represented by Formula (2-1), and the compound represented by Formula (1-2) is represented by Formula (2-2).

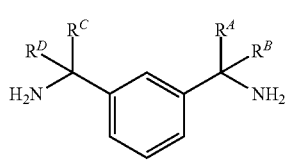

(2-1)

where in Formula (2-1), at least two of $R^A$ to $R^D$ are the same group selected from the group consisting of an ethyl group, an n-propyl group, and an isopropyl group, and the remainder of $R^A$ to $R^D$ is a hydrogen atom, wherein, when two of $R^A$ to $R^D$ are n-propyl groups, Formula (2-1) excludes a case where either $R^A$ or $R^B$, and either $R^C$ or $R^D$ are each an n-propyl group;

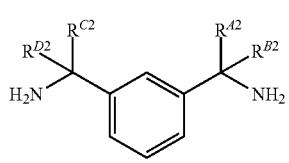

(2-2)

where in Formula (2-2), at least two of $R^{A2}$ to $R^{D2}$ are ethyl groups, and the remainder of $R^{A2}$ to $R^{D2}$ is a hydrogen atom.

<9> The compound production method according to any one of <1> to <7>, wherein at least three of $R^A$ to $R^D$ in Formula (1-1) are ethyl groups, and the remainder of $R^A$ to $R^D$ is a hydrogen atom, and/or at least three of $R^{A2}$ to $R^{D2}$ in Formula (1-2) are ethyl groups, and the remainder of $R^{A2}$ to $R^{D2}$ is a hydrogen atom.

<10> The compound production method according to any one of <1> to <7>, wherein the compound represented by Formula (1-1) and the compound represented by Formula (1-2) are represented by Formula (3) or Formula (4):

[Chem. 8]

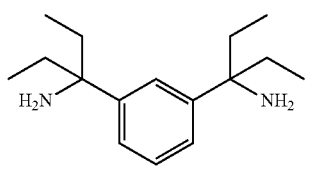

(3)

[Chem. 9]

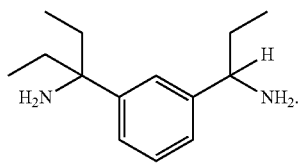

(4)

<11> A compound, represented by Formula (1-1)

[Chem. 10]

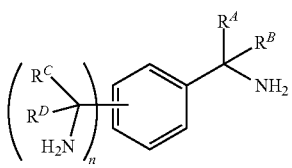

(1-1)

where in Formula (1-1), $R^A$ to $R^D$ each independently represent a hydrogen atom, an ethyl group, an n-propyl group, or an isopropyl group, and n is an integer of from 1 to 3, wherein at least two of $R^A$ to $R^D$ are independently an ethyl group, an n-propyl group, or an isopropyl group, and Formula (1-1) excludes a case where n is 1, a —C($R^C$)($R^D$)(NH$_2$) group is at para position and at meta position, either $R^A$ or $R^B$, and either $R^C$ or $R^D$ are each an n-propyl group, and the remaining two of $R^A$ to $R^D$ are hydrogen atoms; and a case where n is 1, a —C($R^C$)($R^D$)(NH$_2$) group is at ortho position, either $R^A$ or $R^B$, and either $R^C$ or $R^D$ are each an ethyl group, and the remaining two of $R^A$ to $R^D$ are hydrogen atoms.

<12> The compound according to <11>, wherein n in Formula (1-1) is 1.

<13> The compound according to <11>, represented by Formula (2-1).

[Chem. 11]

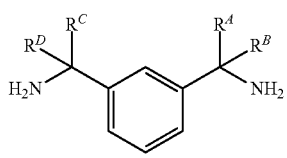

(2-1)

where in Formula (2-1), at least two of $R^A$ to $R^D$ are the same group selected from the group consisting of an ethyl group, an n-propyl group, and an isopropyl group, and the remainder of $R^A$ to $R^D$ is a hydrogen atom, wherein, when two of $R^A$ to $R^D$ are n-propyl groups, Formula (2-1) excludes a case where either $R^A$ or $R^B$, and either $R^C$ or $R^D$ are each an n-propyl group.

<14> The compound according to <11>, represented by Formula (3).

[Chem. 12]

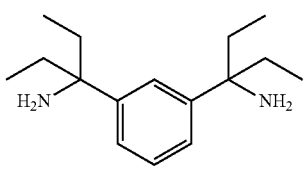

(3)

<15> The compound according to <11>, represented by Formula (4).

[Chem. 13]

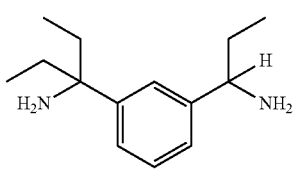

(4)

<16> An epoxy curing agent containing a compound represented by Formula (1').

[Chem. 14]

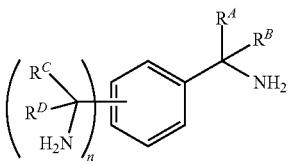

(1')

where in Formula (1'), $R^A$ to $R^D$ each independently represent a hydrogen atom, an ethyl group, an n-propyl group, or an isopropyl group, and n is an integer of from 1 to 3, wherein at least two of $R^A$ to $R^D$ are independently an ethyl group, an n-propyl group, or an isopropyl group.

<17> A method for producing an amine composition containing a compound represented by Formula (1-2), the method comprising filling a compound represented by Formula (5-2) with ethylene and subjecting to alkylation in the presence of a base; wherein a temperature of a reaction solution at the time of the ethylene filling is from 0 to 10° C., and a filling pressure of the ethylene is from 1.5 to 2.3 MPa:

[Chem. 15]

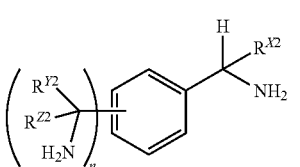

(5-2)

where in Formula (5-2), $R^{X2}$ to $R^{Z2}$ each independently represent a hydrogen atom or an ethyl group, and n is an integer of from 1 to 3;

[Chem. 16]

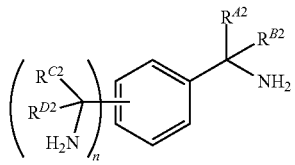

(1-2)

where in Formula (1-2), $R^{A2}$ to $R^{D2}$ each independently represent a hydrogen atom or an ethyl group, and n is an integer of from 1 to 3; wherein at least two of $R^{A2}$ to $R^{D2}$ are ethyl groups.

Advantageous Effects of Invention

The compounds of the present invention excel in storage stability and handleability, and are useful as raw materials and intermediates of organic compounds used as pharmaceuticals, agricultural chemicals, and the like, and as epoxy curing agents.

DESCRIPTION OF EMBODIMENTS

Embodiments of the present invention (hereinafter, referred to as "present embodiment") are described in detail below; however, the present invention is not limited to the embodiments, and various modifications may be made without departing from the scope and spirit of the invention.

Note that, in the present specification, " . . . to . . . " is used to mean that the numerical values given before and after the "to" are included as the lower limit and the upper limit, respectively.

Compound

The compound of the present embodiment is a compound represented by Formula (1-1). The compound of the present embodiment is not particularly limited as long as it is a compound represented by Formula (1-1), and it may be one or a mixture of two.

The compound represented by Formula (1-1) is useful as an intermediate of a compound used in pharmaceuticals, agricultural chemicals, and the like, and as an epoxy curing agent.

[Chem. 17]

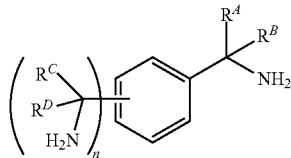

(1-1)

where in Formula (1-1), $R^A$ to $R^D$ each independently represent a hydrogen atom, an ethyl group, an n-propyl group, or an isopropyl group, and n is an integer of from 1 to 3.

However, at least two of $R^A$ to $R^D$ are each independently an ethyl group, an n-propyl group, or an isopropyl group. In addition, Formula (1-1) excludes a case where n is 1, a —$C(R^C)(R^D)(NH_2)$ group is at the para position and at the meta position, either $R^A$ or $R^B$, and either $R^C$ or $R^D$ are each an n-propyl group, and the remaining two of $R^A$ to $R^D$ are hydrogen atoms; and a case where n is 1, a —$C(R^C)(R^D)(NH_2)$ group is at the ortho position, either $R^A$ or $R^B$, and either $R^C$ or $R^D$ are each an ethyl group, and the remaining two of $R^A$ to $R^D$ are hydrogen atoms.

where in Formula (1-1), n is an integer of from 1 to 3, and is preferably 1 or 2, and more preferably 1. When n is 1, the —$C(R^C)(R^D)(NH_2)$ group may located at any of the ortho, meta, or para positions, but is preferably at the meta position.

At least two of the $R^A$ to $R^D$ are preferably an ethyl group, n-propyl group, or isopropyl group, and are preferably the same group selected from the group consisting of an ethyl group, an n-propyl group, and an isopropyl group. Furthermore, at least two of $R^A$ to $R^D$ are preferably ethyl groups.

The compound represented by Formula (1-1) is preferably represented by Formula (2-1).

[Chem. 18]

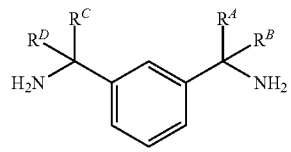

(2-1)

where in Formula (2-1), at least two of $R^A$ to $R^D$ are the same group selected from the group consisting of an ethyl group, an n-propyl group, and an isopropyl group, and the remainder of $R^A$ to $R^D$ is a hydrogen atom.

However, when two of $R^A$ to $R^D$ are n-propyl groups, Formula (2-1) excludes a case where either $R^A$ or $R^B$, and either $R^C$ or $R^D$ are each an n-propyl group.

In Formula (1-1), "a case in which n is 1, a —$C(R^C)(R^D)(NH_2)$ group is at the para position, either $R^A$ or $R^B$, and either $R^C$ or $R^D$ are each an n-propyl group, and the remaining two of $R^A$ to $R^D$ are hydrogen atoms" means specifically the following compound.

[Chem. 19]

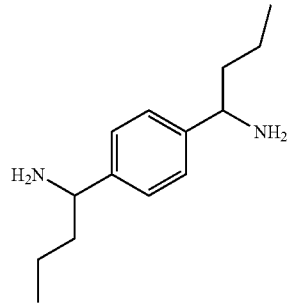

In Formula (1-1), "a case where n is 1, a —$C(R^C)(R^D)(NH_2)$ group is at the meta position, either $R^A$ or $R^B$, and either $R^C$ or $R^D$ are each an n-propyl group, and the remaining two of $R^A$ to $R^D$ are hydrogen atoms", and in Formula (2-1), "a case where, when two of $R^A$ to $R^D$ are n-propyl groups, either $R^A$ or $R^B$, and either $R^C$ or $R^D$ are each an n-propyl group" mean specifically the following compound.

[Chem. 20]

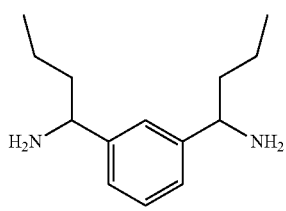

In Formula (1-1), "a case where n is 1, a —C($R^C$)($R^D$)($NH_2$) group is at the ortho position, either $R^A$ or $R^B$, and either $R^C$ or $R^D$ are each an ethyl group, and the remaining two of $R^A$ to $R^D$ are hydrogens" means specifically the following compound.

[Chem. 21]

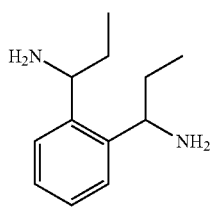

An example of a compound of the present embodiment is an aspect of a compound represented by Formula (1-1), wherein three or more of $R^A$ to $R^D$ are each independently an ethyl group, an n-propyl group, or an isopropyl group. Another aspect of a compound represented by Formula (1-1) is a compound for which n is 1, and three or four of $R^A$ to $R^D$ are each independently an ethyl group, an n-propyl group, or an isopropyl group. Such compounds are readily obtained in the presence of a base composition and by splitting the base composition such that the base composition is divided into two or more portions and introduced into the reaction system.

Specific examples of the compound represented by Formula (1-1) include the following compounds.

[Chem. 22]

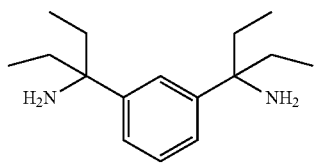

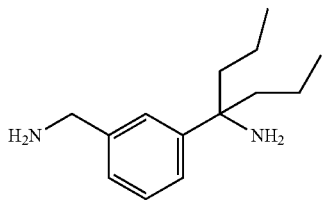

(3)

[Chem. 23]

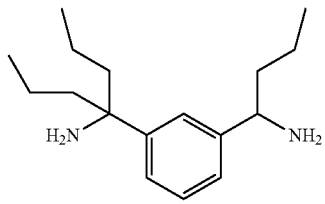

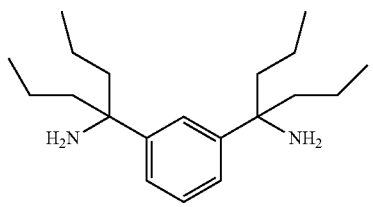

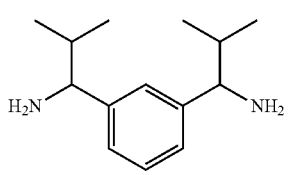

[Chem. 24]

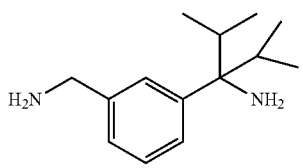

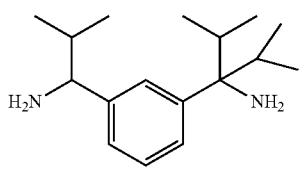

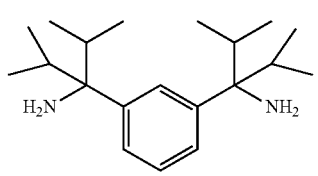

(4)

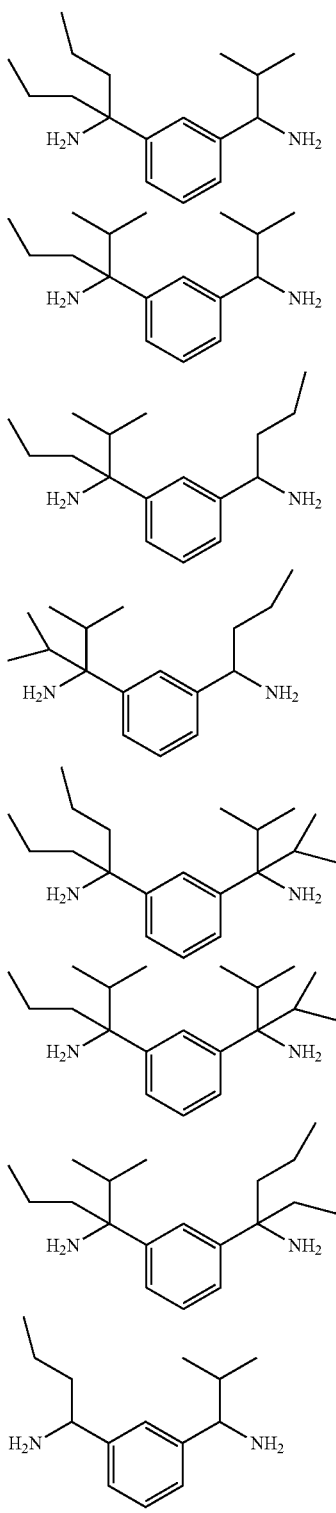

Among the specific compounds described above, compounds represented by Formula (3) and Formula (4) are preferable.

The molecular weight of the compound represented by Formula (1-1) is preferably more than or equal to 160, more preferably more than or equal to 180, and even more preferably more than or equal to 190. The molecular weight of the compound represented by Formula (1-1) is preferably less than or equal to 500, more preferably less than or equal to 350, and even more preferably less than or equal to 250.

The compound of the present embodiment may be purified and used as a single compound, or may be a composition containing one or more types of compounds represented by Formula (1-1). Examples thereof include a composition containing a compound represented by Formula (3) and a compound represented by Formula (4). Furthermore, an example of a composition of the present embodiment is a composition that contains a compound represented by Formula (3) and a compound represented by Formula (4), wherein a total proportion of compounds represented by Formula (1-1) and for which one or two of $R^A$ to $R^D$ are an ethyl group, an n-propyl group, or an isopropyl group, and the remainder of $R^A$ to $R^D$ is a hydrogen atom is 20 mass % or less of the total amount of the compounds represented by Formula (3) and the compounds represented by Formula (4).

[Compound Production Method]

The compound production method of a first embodiment is a method for producing a compound represented by Formula (1-1), the method including a step of subjecting a compound represented by Formula (5-1) to an addition reaction to add ethylene and/or propylene in the presence of a base.

[Chem. 26]

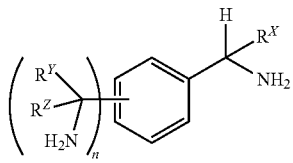

(5-1)

where in Formula (5-1), $R^X$ to $R^Z$ each independently represent a hydrogen atom, an ethyl group, an n-propyl group, or an isopropyl group, and n is an integer of 1 to 3.

With respect to $R^X$ to $R^Z$ in Formula (5-1), n is an integer of from 1 to 3, and is preferably 1. When n is 1, the —C($R^Y$)($R^Z$)($NH_2$) group may be located at any of the ortho, meta, or para positions, but is preferably at the meta position.

$R^X$ to $R^Z$ are preferably all hydrogen atoms.

The compound represented by Formula (5-1) is preferably meta-xylylenediamine. The meta-xylylenediamine is also abbreviated herein as MXDA.

The compound represented by Formula (5-1) may be prepared by a known organic reaction, or may be obtained as a commercially available product.

The compound represented by Formula (5-1) preferably includes specifically a compound selected from the group consisting of benzylamine, α-methyl benzenemethanamine, α-ethyl benzenemethanamine, o-xylylenediamine, m-xylylenediamine, p-xylylenediamine, 1,2,3-benzene trimethanamine, 1,2,4-benzene trimethanamine and 1,2,4,5-benzene tetramethanamine, and more preferably includes m-xylylenediamine.

One type of the compound represented by Formula (5-1) may be used alone, or two or more types may be used. When two or more types are used, an obtained compound represented by Formula (1-1) also forms a mixture.

The ratio of ethylene and/or propylene to the compound represented by Formula (5-1) may be appropriately adjusted according to the amount of ethylene and/or propylene that is added. As a molar ratio, the ratio of ethylene and/or propylene to the compound represented by Formula (5-1) is typically in a range from 0.01 to 20, and preferably from 0.1 to 10, relative to 1 mole of the compound represented by Formula (5-1).

Furthermore, ethylene and/or propylene may be added as an addition during the reaction, or may be added continuously during the reaction.

The added amount of base in the production method of the present embodiment is generally from 0.01 to 400 mass %, preferably from 0.1 to 300 mass %, and more preferably from 1.0 to 150 mass %, relative to the mass of the compound represented by Formula (5-1), which is a raw material.

The reaction temperature may be suitably adjusted according to the type of the substrate to be reacted or the like, and is typically in a range from 0 to 150° C., and preferably from 10 to 120° C. By setting the temperature to 10° C. or higher, a more sufficient reaction rate is obtained, and the selectivity tends to further improve. By setting the temperature to not more than 120° C., by-products such as tar content can be reduced, which is more preferable.

The reaction pressure is sufficient as long as the pressure is a pressure that is necessary for the compound represented by Formula (5-1) and the product to be substantially present as liquids under the reaction conditions, and in terms of absolute pressure, the reaction pressure is preferably in a range from 0.05 to 50 atm, and more preferably from 0.1 to 40 atm.

Examples of the reaction method include a method in which raw materials are supplied in a batch manner or a semi-batch manner to a reaction vessel charged with a base, a fully mixed circulation method in which a base and raw materials are continuously supplied to the reaction vessel, and a fixed bed circulation method in which the reaction vessel is filled with a base, and the raw materials are circulated. The reaction method can be selected appropriately according to the type of reaction product that is targeted, but a batch method is preferable. By using a batch method, the operation for carrying out the reaction is not complicated, deactivation of the base due to moisture contamination can be suppressed, and the activity of the base can be more effectively maintained.

The reaction time of the addition reaction is typically from 0.1 to 10 hours as a reaction time with the batch method or semi-batch method, or as a residence time with the fully mixed circulation method. In the case of the fixed bed circulation method, 0.1 to 10 $h^{-1}$ is typically adopted as the LSV of the compound represented by Formula (5-1).

(Base)

The base used in the production method of the present embodiment is not particularly limited as long as the base functions as a catalyst for the reaction in which ethylene and/or propylene is added to the compound represented by Formula (5-1). The base is preferably a base containing at least one type of alkali metal, and is more preferably a base containing at least one type of alkali metal selected from the group consisting of sodium, rubidium, and cesium. The alkali metal-containing compound (A) is preferably $M^aOH$ or $M^a_2CO_3$ ($M^a$ is an alkali metal).

Specific examples of the base include a base composition A derived from a composition containing: one or more types of alkali metal-containing compounds (A) selected from the group consisting of rubidium carbonate, rubidium hydroxide, cesium carbonate, and cesium hydroxide; and a metallic sodium (B).

Specifically, the base composition A is obtained by heat treating a composition containing the alkali metal-containing compound (A) and the metallic sodium (B) in an inert gas atmosphere. Furthermore, the base composition A is a heat-treated product of a mixture of the alkali metal-containing compound (A) and the metallic sodium (B). In the mixture, the metallic sodium and the one or more types of alkali metal-containing compounds (A) selected from the group consisting of rubidium carbonate, rubidium hydroxide, cesium carbonate, and cesium hydroxide are preferably present in the same system.

The alkali metal-containing compound (A) in the base composition A is rubidium carbonate, rubidium hydroxide, cesium carbonate, and cesium hydroxide. Among these alkali metal-containing compounds (A), from the perspective of further increasing the activity as a catalyst that promotes a reaction of adding ethylene and/or propylene to the compound represented by Formula (5-1), the alkali metal-containing compound (A) is preferably rubidium carbonate or cesium carbonate, and is more preferably cesium carbonate. One type of these alkali metal-containing compounds (A) may be used alone, or a combination of two or more types may be used.

From the perspective of efficiently advancing the reaction, the ratio of the substance amount of rubidium and/or cesium contained in the alkali metal-containing compound (A) in the base composition A to the substance amount of the metallic sodium (B) ((substance amount of rubidium and/or cesium):(substance amount of sodium) (molar ratio)) is from 0.50:1 to 8.0:1, preferably from 1.0:1 to 4.0:1, more preferably from 1.0:1 to 3.0:1, and even more preferably from 1.5:1 to 2.5:1.

With respect to the base composition A, the composition containing the alkali metal-containing compound (A) and the metallic sodium (B) preferably further contains an alkaline earth metal compound (compound containing a Group 2 element of the periodic table). The alkaline earth metal compound (C) is more preferably $M^c(OH)_2$, $M^cCO_3$, or $M^cO$ ($M^c$ is an alkaline earth metal), and the composition containing the alkali metal-containing compound (A) and the metallic sodium (B) even more preferably contains one or more types of alkaline earth metal compounds selected from the group consisting of magnesium oxide, magnesium hydroxide, and magnesium carbonate. By containing the alkaline earth metal compound (C), stickiness of the base composition A can be suppressed, and handleability can be improved.

When the total amount of the alkali metal-containing compound (A) and the metallic sodium (B) is 100 parts by mass, the content of the alkaline earth metal compound (C) (preferably a magnesium compound) is preferably 30 parts by mass or more, more preferably 40 parts by mass or more, even more preferably 50 parts by mass or more, and yet even more preferably 60 parts by mass or more. The upper limit is preferably not more than 150 parts by mass, more preferably not more than 130 parts by mass, and even more preferably not more than 100 parts by mass. When the content of the alkaline earth metal compound (C) is not less than 30 parts by mass, stickiness of the base composition A tends to be suppressed. In addition, when the content of the alkaline earth metal compound (C) is not more than 150 parts by mass, the reaction tends to proceed without affecting the activity of the base composition A as a catalyst.

The base composition A can be produced by heat treating a mixture containing one or more types of alkali metal-containing compounds (A) selected from the group consisting of rubidium carbonate, rubidium hydroxide, cesium carbonate, and cesium hydroxide, and the metallic sodium (B) at a temperature from 100° C. and to 500° C. in an inert gas atmosphere. The order in which the alkali metal-containing compound (A) and the metallic sodium (B) are mixed is not particularly limited.

Examples of the inert gas include helium, nitrogen, and argon.

The temperature when preparing the base composition A is preferably from 98° C. to 500° C., more preferably from 110° C. to 300° C., and even more preferably from 120° C. to 280° C. When the temperature is from 98° C. to 500° C., the metallic sodium melts and therefore tends to be easily dispersed and mixed, and also tends to be sufficiently fired to form a highly active catalyst.

The heating time when preparing the base composition A is preferably from 10 minutes to 5 hours, more preferably from 30 minutes to 3 hours, and even more preferably from 30 minutes to 2 hours. When the heating time is from 10 minutes to 5 hours, the catalyst is sufficiently fired, and tends to become a highly active catalyst.

The alkaline earth metal compound (C) may be added to the mixture of the alkali metal-containing compound (A) and the metallic sodium (B), and the order in which the alkali metal containing compound (A), the metallic sodium (b), and the alkaline earth metal compound (C) are mixed is not particularly limited.

Because the alkali metal-containing compound (A) and the alkaline earth metal compound (C) have high hygroscopicity, heat treatment may be performed before the preparation of the base composition A. The heat treatment before preparation is preferably performed under an inert gas or vacuum conditions. The temperature of the heat treatment before preparation is not particularly limited as long as it is a temperature at which unnecessary moisture can be removed, and is normally from 200° C. to 500° C., and preferably from 250° C. to 400° C.

When the heat treatment temperature is set from 200° C. to 500° C., moisture in the compound can be sufficiently removed, and the formation of a highly active catalyst tends to occur. The heat treatment time before preparation is preferably from 10 minutes to 5 hours, more preferably from 30 minutes to 3 hours, and even more preferably from 30 minutes to 2 hours. When the heating time is set to a range from 10 minutes to 5 hours, moisture can be sufficiently removed, and a highly active catalyst tends to be formed.

After the reaction is completed, the reaction solution and the base composition can be separated by an ordinary method such as fractional sedimentation, centrifugation, or filtration.

The base composition acts as a catalyst in the synthesis reaction of the compound of the present embodiment, but also functions as an irreversible reaction initiator. Thus, the amount of the base composition in the system decreases as the synthesis reaction of the amine compound proceeds. Therefore, in the synthesis reaction of the compound of the present embodiment, the base composition is preferably divided into two or more portions and then added. The upper limit of the number of portions in which the base composition is added is not particularly limited, but 10 portions or less is practical. Furthermore, the addition of ethylene and/or propylene to three or more, particularly three or four, and more particularly four of $R^X$ to $R^Z$ of the compound represented by Formula (5-1) is facilitated.

The base composition may also be introduced into the reaction solution continuously or intermittently at a constant rate. The rate of introduction may be constant or may be varied over time.

The addition reaction of the production method of the present embodiment may be carried out in the presence or absence of a solvent. The solvent is appropriately selected according to the reaction temperature, the reaction product, and the like. Examples of the solvent include tetrahydrofuran, diethyl ether, dibutyl ether, 1,4-dioxane, 1,3,5-trioxane, 1,2-dimethoxyethane, and diethylene glycol dimethyl ether.

When a solvent is used in the organic reaction described above, the obtained reaction solution may be concentrated as necessary, after which the residue may be used as is as the compound represented by Formula (1-1), and after a post-treatment is performed as appropriate, the treated residue may be used as a compound represented by Formula (1-1). Specific examples of the method of the post-treatment include well-known purification methods, such as distillation and chromatography.

Note that in the examples described below, only examples of ethylene addition are presented, but it is known that the mechanisms of ethylene addition and propylene addition are the same, and the reactions proceed in nearly the same manner.

A method for producing a compound of a second embodiment is a method for producing a compound represented by Formula (1-2), the method including filling a compound represented by Formula (5-2) with ethylene and subjecting to alkylation in the presence of a base; wherein a temperature of a reaction solution at the time of ethylene filling is from 0 to 10° C., and a filling pressure of the ethylene is from 1.5 to 2.3 MPa.

[Chem. 27]

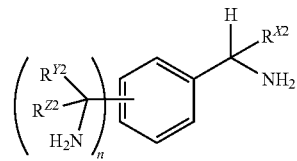

(5-2)

where in Formula (5-2), $R^{X2}$ to $R^{Z2}$ each independently represent a hydrogen atom or an ethyl group, and n is an integer of from 1 to 3.

[Chem. 28]

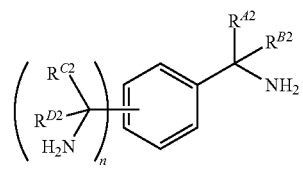

(1-2)

where in Formula (1-2), $R^{A2}$ to $R^{D2}$ each independently represent hydrogen or an ethyl group, and n is an integer of from 1 to 3. However, at least two of $R^{A2}$ to $R^{D2}$ are ethyl groups.

In addition, in Formula (1-2), a case where n is 1, a —C($R^{C2}$)($R^{D2}$)(NH$_2$) group is at the Ortho position, either $R^{A2}$ or $R^{B2}$, and either $R^{C2}$ or $R^{D2}$ are each an ethyl group, and the remaining two of $R^{A2}$ to $R^{D2}$ are hydrogens is preferably excluded.

A compound represented by Formula (1-2), and in particular, a compound in which ethylene is added at a high frequency to the carbon atoms of aminomethyl groups as presented below, can be obtained.

[Chem. 29]

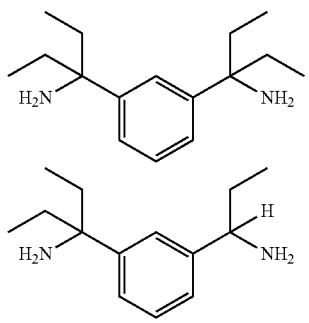

In the production method of the present embodiment, the temperature of the reaction solution at the time of ethylene filling is from 0 to 10° C., and the filling pressure of ethylene is from 1.5 to 2.3 MPa. By setting the temperature of the reaction solution at the time of ethylene filling to not more than 10° C., the active species generated in the initial stage of the reaction can be stably handled. Furthermore, the addition reaction of ethylene tends to proceed when the filling pressure of ethylene is set to 2.3 MPa or less. Moreover, when the temperature of the reaction solution at the time of ethylene filling is set to 0° C. or higher, the time required for the temperature to increase to the reaction temperature can be shortened, and thus the reaction performance can be improved. Moreover, setting the filling pressure of the ethylene to not less than 1.5 MPa makes it possible to effectively promote the ethylene addition reaction.

With the production method of the present embodiment, filling with ethylene gas is typically implemented.

The lower limit of the temperature of the reaction solution when filling with ethylene is preferably 1° C. or higher, and more preferably 2° C. or higher. In addition, the upper limit of the temperature of the reaction solution is preferably 8° C. or lower, more preferably 6° C. or lower, even more preferably 5° C. or lower, and yet even more preferably 4° C. or lower.

The temperature of the reaction solution in the present invention means the liquid temperature of the reaction solution when filling with ethylene gas.

The lower limit of the pressure when filling with ethylene (ethylene filling pressure) is preferably 1.7 MPa or higher, more preferably 1.8 MPa or higher, and even more preferably 1.9 MPa or higher. The upper limit of the pressure when filling with ethylene is preferably not more than 2.2 MPa and more preferably not more than 2.1 MPa.

In the production method of the present embodiment, alkylation (ethylene addition) proceeds through ethylene.

For example, the lower limit of the temperature of the reaction system after ethylene filling is preferably higher than 10° C., more preferably 12° C. or higher, even more preferably 14° C. or higher, yet even more preferably 16° C. or higher, and still even more preferably 18° C. or higher. Furthermore, the upper limit of the temperature of the reaction system after ethylene filling is preferably 35° C. or lower, more preferably 30° C. or lower, and even more preferably 25° C. or lower.

In the production method of the present embodiment, the difference between the temperature of the reaction system at the time of ethylene filling and after ethylene filling is preferably at least 10° C., and more preferably from 10 to 20° C. The ethylene addition reaction proceeds more effectively by adopting such a constitution.

The time of the ethylene addition reaction is preferably from 1 to 100 hours, and more preferably from 10 to 60 hours. As described in detail below, when the base is divided into two or more portions so as to be introduced into the reaction system in each portion, the total is preferably within the range described above.

The ratio of ethylene to the compound represented by Formula (5-2) may be adjusted, as appropriate, in accordance with the amount of ethylene addition, but the molar ratio of ethylene to 1 mole of the compound represented by Formula (5-2) is preferably in a range from 1 to 30, more preferably from 3 to 20, and even more preferably from 4 to 15.

Unless otherwise specified, the reaction method can be performed in the same manner as described in the first embodiment, and the solvents and other conditions are the same as those of the first embodiment, and the preferred ranges are also the same.

<Compound Represented by Formula (1-2)>

[Chem. 30]

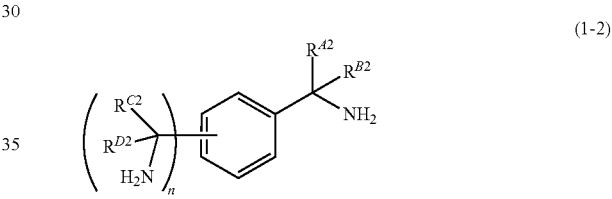

(1-2)

where in Formula (1-2), $R^{A2}$ to $R^{D2}$ each independently represent a hydrogen atom or an ethyl group, and n is an integer of from 1 to 3. However, at least two of $R^{A2}$ to $R^{D2}$ are ethyl groups.

In Formula (1-2), n is the same as n in Formula (1-1), and the preferred range is also the same.

More preferably, in Formula (1-2), at least three of $R^{A2}$ to R' are ethyl groups, and the remainder of $R^{A2}$ to $R^{D2}$ is a hydrogen atom.

The compound represented by Formula (1-2) is preferably represented by Formula (2-2).

[Chem. 31]

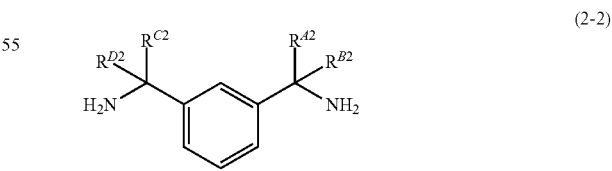

(2-2)

where in Formula (2-2), at least two of $R^{A2}$ to $R^{D2}$ are ethyl groups, and the remainder of $R^{A2}$ to $R^{D2}$ is a hydrogen atom.

More preferably, in Formula (2-2), three or four (and more preferably four) of $R^{A2}$ to $R^{D2}$ are ethyl groups and the remainder of $R^{AZ}$ to $R^{D2}$ is a hydrogen atom.

The molecular weight of the compound represented by Formula (1-2) is preferably more than or equal to 160, more preferably more than or equal to 180, and even more preferably more than or equal to 190. The molecular weight thereof is preferably not more than 400, more preferably not more than 300, and even more preferably not more than 250.

Examples of compounds represented by Formula (1-2) are shown below. Of course, the present invention is not limited to these compounds.

[Chem. 32]

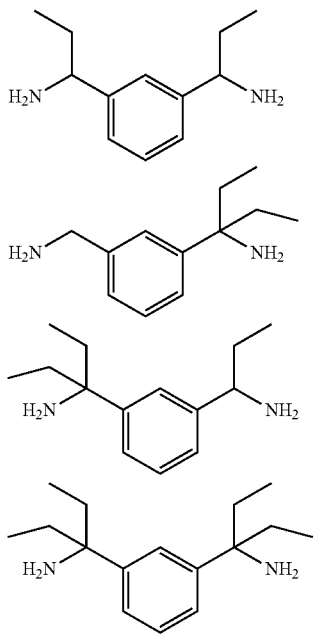

<Compound Represented by Formula (5-2)>

[Chem. 33]

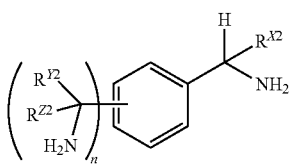

where in Formula (5-2), $R^{X2}$ to $R^{Z2}$ each independently represent a hydrogen atom or an ethyl group, and n is an integer of from 1 to 3.

One type of compound represented by Formula (5-2) may be used alone, or two or more types may be used. When two or more types are used, the obtained compound represented by Formula (1-2) also becomes mixture.

<Base>

In the production method of the present embodiment, the compound represented by Formula (5-2) is alkylated in the presence of a base.

The base also functions as an irreversible reaction initiator while acting as a catalyst in the ethylene addition reaction. Thus, the amount of base in the system decreases as the ethylene addition reaction progresses. Therefore, in the production method of the present embodiment, the base is preferably divided into two or more portions and introduced into the reaction system. The upper limit of the number of portions in which the base is added is not particularly limited, but 10 portions or less is practical. By dividing and adding the base in this manner, the addition of ethylene to three or more, particularly three or four, and more particularly four of $R^{A2}$ to $R^{D2}$ of the compound represented by Formula (5-2) is facilitated.

When the base is divided into two or more portions and introduced into the reaction system, filling and alkylation of the ethylene gas is preferably performed each time. That is, filling with ethylene and subjecting to alkylation in the presence of a base is preferably repeated two or more times.

The base may also be continuously or intermittently introduced into the reaction solution at a constant rate. The rate of introduction may be constant or may be varied over time.

The mass of the base in the production method of the present embodiment is generally from 0.001 to 10 parts by mass, preferably from 0.005 to 5 parts by mass, more preferably from 0.01 to 4 parts by mass, and even more preferably from 0.05 to 3 parts by mass, per 1 part by mass of the compound represented by Formula (5-2). When the addition of the base is divided into multiple portions, the total amount of the base is preferably within the range described above.

A specific example of the base that can be preferably used is, in particular, a base composition A containing: one or more types of alkali metal-containing compounds (A) selected from the group consisting of rubidium carbonate, rubidium hydroxide, cesium carbonate, and cesium hydroxide, and a metallic sodium (B). The details of the base composition A are the same as described with regard to the production method of the first embodiment.

After the reaction is completed, the reaction solution and the base composition A can be separated by an ordinary method such as fractional sedimentation, centrifugation, or filtration.

[Amine Composition and Production Method Thereof]

With the method for producing the compound represented by Formula (1-1) and the method for producing the compound represented by Formula (1-2), the obtained compound may be purified and used as a single compound, or may be an amine composition containing one or more types of the compound represented by Formula (1-1) and the compound represented by Formula (1-2).

That is, an example of a method for producing an amine composition according to the present embodiment includes a method for producing an amine composition containing a compound represented by Formula (1-2), the method including filling a compound represented by Formula (5-2) with ethylene and subjecting to alkylation in the presence of a base, with the temperature of the reaction solution at the time of the ethylene filling being from 0 to 10° C., and the filling pressure of the ethylene being from 1.5 to 2.3 MPa. In the method for producing the amine composition, the compound represented by Formula (5-2), the compound represented by Formula (1-2), and the various conditions such as ethylenation are the same as with the method for producing the compound represented by Formula (1-1) above, and the preferable ranges are the same.

In the method for producing the amine composition of the present embodiment, an amine composition containing two or more types of compounds represented by Formula (1-2) is obtained.

Furthermore, in the present embodiment, an amine composition is exemplified in which a total proportion of compounds represented by Formula (2-2) and for which three or four of $R^{A2}$ to $R^{D2}$ are ethyl groups is 80 mass % or more (preferably 90 mass % or more) of the total amount of the compounds represented by Formula (2-2).

Furthermore, in the present embodiment, an amine composition is exemplified in which a total proportion of compounds represented by Formula (2-2) and for which four of $R^{A2}$ to $R^{D2}$ are ethyl groups is 80 mass % or more (preferably 90 mass % or more) of the total amount of the compounds represented by Formula (2-2).

[Epoxy Curing Agent]

The epoxy curing agent of the present embodiment contains a compound represented by Formula (1'). The epoxy curing agent of the present embodiment excels in storage stability and handleability.

[Chem. 34]

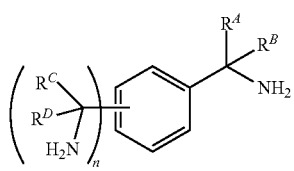

(1')

In Formula (1'), $R^A$ to $R^D$ and n are synonymous with the $R^A$ to $R^D$ and n in Formula (1-1). In other words, in Formula (1'), $R^A$ to $R^D$ each independently represent a hydrogen atom, an ethyl group, an n-propyl group, or an isopropyl group, and n is an integer of from 1 to 3. However, at least two of $R^A$ to $R^D$ are independently an ethyl group, an n-propyl group, or an isopropyl group.

In Formula (1'), preferred aspects of $R^A$ to $R^D$ and n and preferred aspects of the substitution position of the —C($R^C$)($R^D$)(NH$_2$) group are the same as those in Formula (1-1).

The compound represented by Formula (1') is preferably represented by Formula (2').

[Chem. 35]

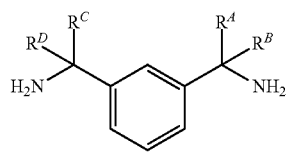

(2')

$R^A$ to $R^D$ in Formula (2') is the same as $R^A$ to $R^D$ in Formula (2-1). In other words, in Formula (2'), at least two of $R^A$ to $R^D$ are the same group selected from the group consisting of an ethyl group, an n-propyl group, and an isopropyl group, and the remainder of $R^A$ to $R^D$ is a hydrogen atom.

Specific examples of the compounds included in the epoxy curing agent of the present embodiment include the following compounds.

[Chem. 36]

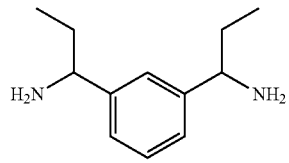

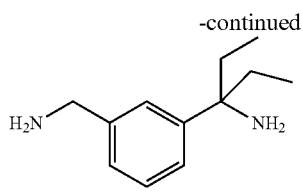

(4)

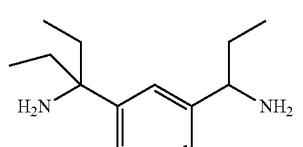

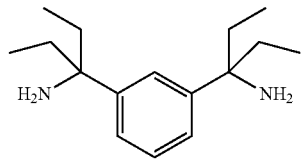

(3)

[Chem. 37]

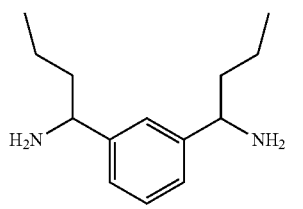

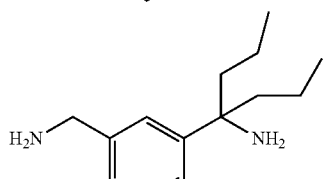

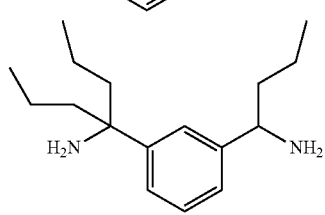

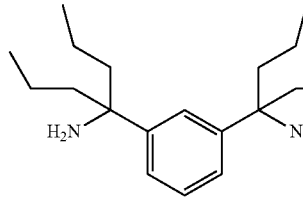

[Chem. 38]

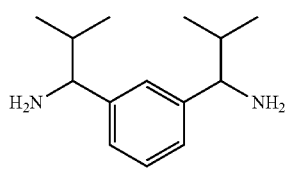

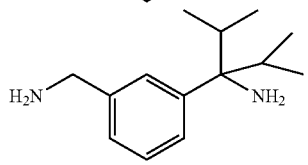

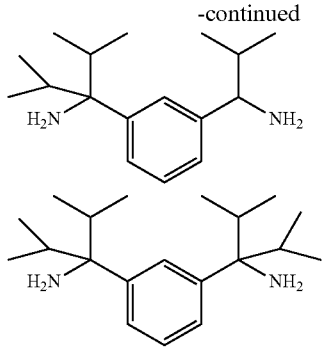

[Chem. 39]

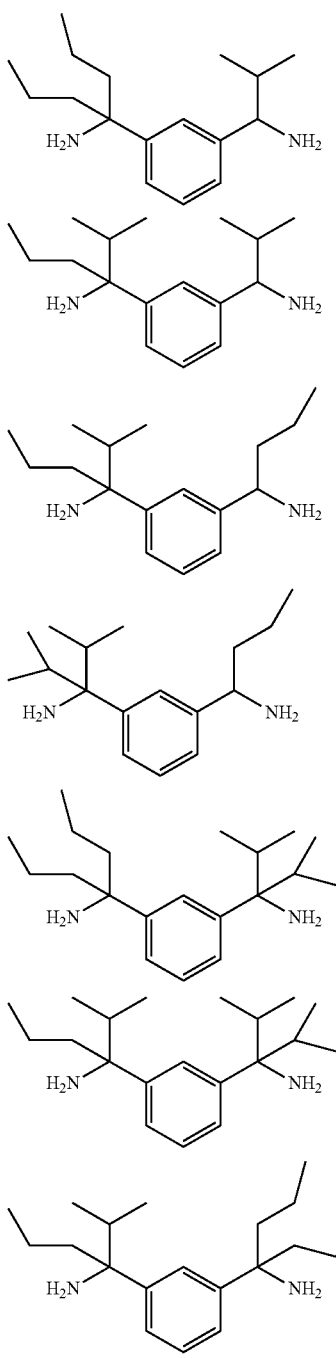

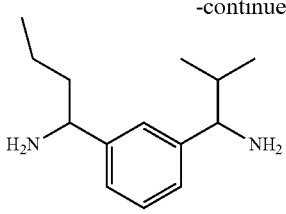

The compound represented by Formula (3) and the compound represented by Formula (4) are preferable as the compound included in the epoxy curing agent of the present embodiment.

The epoxy curing agent may be used in combination with an amine compound other than the compound represented by Formula (1') and may also contain additives such as known curing accelerators and diluents, in a range that does not affect the reaction with the epoxy resin. As the known curing agent, an amine-based curing agent described in paragraph [0029] of JP 6177331 B and an amine-based curing agent described in paragraphs [0011] to [0016] of JP 2011-213983 A, the contents of which are incorporated herein, can be referenced.

The compound represented by Formula (1') in the above-mentioned epoxy curing agent is preferably a main component of the components constituting the epoxy curing agent. When a main component, the content of the compound represented by Formula (1') is ordinarily not less than 50 mass %, preferably not less than 70 mass %, more preferably not less than 80 mass %, even more preferably not less than 90 mass %, yet even more preferably not less than 95 mass %, and still even more preferably not less than 98 mass %. The upper limit of the content of the compound represented by Formula (1') contained in the epoxy curing agent is 100 mass %.

[Epoxy Resin Composition]

The epoxy resin composition of the present embodiment preferably contains the abovementioned epoxy resin curing agent and an epoxy resin.

The epoxy resin in which the epoxy curing agent of the present embodiment is used is not particularly limited as long as the epoxy resin is a compound having an epoxy group.

Per molecule, the epoxy resin ordinarily has from 2 to 10 epoxy groups, preferably from 2 to 6 epoxy groups, more preferably from 2 to 4 epoxy groups, and even more preferably 2 epoxy groups. The epoxy group is preferably a glycidyl ether group. The epoxy resin may be a low molecular weight compound (for example, a number average molecular weight of less than 2000) or a high molecular weight compound (polymer, for example, a number average molecular weight of 2000 or more). The epoxy resin of the polymer may be an aliphatic compound, an alicyclic compound, or a compound having an aromatic ring. In particular, the epoxy resin preferably has, per molecule, two aromatic rings and/or two six-membered aliphatic rings, and more preferably has two aromatic rings per molecule. Among these, epoxy resins obtained through a reaction between epichlorohydrin and a compound having two or more reactive hydrogen atoms (for example, a polyol) are preferable. Specific examples of the raw materials of the epoxy resin include bisphenol A (2,2-bis(4-hydroxyphenyl)propane) or a hydride thereof, bisphenol F (4,4'-dihydroxydiphenylmethane), or a hydride thereof, tetrabromobisphenol A (2,2-bis(3,5-dibromo-4-hydroxyphenyl)propane) or a hydride thereof, a novolac resin in which cresol is reacted with formaldehyde, hexahydrophthalic acid, and the like. As the epoxy resin that can be used in the epoxy resin composition, in addition to the above, the disclosures of paragraphs [0036] to [0039] of JP 2018-83905 A, and paragraphs [0032] to [0035] of JP 2018-135433 A, the contents of which are incorporated herein, can be referenced.

The content of the epoxy resin in the epoxy resin composition is preferably not less than 79 mass %, more preferably not less than 81 mass %, and even more preferably not less than 82 mass %, in the solid content not including the diluent. The upper limit is preferably 89 mass % or less, more preferably 87 mass % or less, and even more preferably 86 mass % or less.

In the total amount of the epoxy resin composition containing the diluent, the content of the epoxy resin is preferably not less than 76 mass %, more preferably not less than 79 mass %, and even more preferably not less than 81 mass %. The upper limit is preferably 90 mass % or less, more preferably 87 mass % or less, and even more preferably 85 mass % or less.

One type of epoxy resin may be used, or a plurality of types may be used. When a plurality of epoxy resins are used, the total amount thereof is within the range described above.

The epoxy resin composition may contain components other than the epoxy resin and curing agent. Specific examples of other components that may be contained include reactive diluents, non-reactive diluents, curing accelerators, plasticizers, pigments, dyes, fillers, release agents, toughening agents, antioxidants, UV absorbers, photostabilizers, fluidizers, leveling agents, defoaming agents, flame retardants, or thickeners.

A cured product according to the present embodiment is formed from the epoxy resin composition. The cured product can be used in a wide range of fields, such as in architectural paints, adhesives, automotive components, aircraft components, composite materials, printed circuit board materials, insulating impregnated materials of a heavy electrical machinery, and sealing materials for electronic devices. In addition, the cured product is preferably used in the applications described in paragraph [0045] of JP 2018-83905 A, paragraph [0053] of JP 2018-135433 A, paragraph [0039] to [0043] of JP 2016-527384 T, and paragraph [0048] of JP 2011-213983 A, the contents of which are incorporated herein.

[Polyurethane Urea Resin Composition]

The amine compound represented by Formula (1-1) can be used as a curing agent for curing a urethane prepolymer. Furthermore, a polyurethane urea resin composition of the present embodiment preferably contains the abovementioned urethane prepolymer curing agent and a urethane prepolymer.

The cured product according to the present embodiment is formed from a polyurethane urea resin composition.

EXAMPLES

The present invention will be described in further detail hereinafter using examples and comparative examples, but the present invention is not limited to the following examples. Note that amino group-containing alkyl substituted aromatic compounds were analyzed by the following method.

[Analysis of Amino Group-Containing Alkyl Substituted Aromatic Compounds]

(1) Gas Chromatography (Hereinafter, GC Analysis)
Device; GC-2025 available from Shimadzu Corporation
Column; CP-Sil 8 CB for Amines (0.25 μm×0.25 mm×30 m), available from Agilent Technologies, Inc.
Column temperature: Maintained for 2 minutes at 80° C., subsequently heated at a rate of 8° C./minute, and then maintained for 5 minutes at 150° C., and subsequently heated at a rate of 15° C./minute, and then maintained for 5 minutes at 300° C.

(2) Time-of-Flight Mass Spectrometry (Hereinafter, TOFMS Analysis)
Device; AccuTOF GCX, available from JEOL, Ltd.
Ionization technique; FI$^+$ (3) Nuclear Magnetic Resonance Absorption ($^1$H NMR, $^{13}$C NMR)

Measurements were performed in a deuterium-substituted chloroform solvent using the AVANCE II 600 MHz nuclear magnetic resonance apparatus available from Bruker Corporation. Note that δ (ppm) described below indicates a chemical shift represented by the following equation.

δ (ppm)=$10^6$×($v_S$−$v_R$)/$v_R$ $v_S$: Resonance frequency (Hz) of the sample
$v_R$: Resonance frequency (Hz) of trimethylsilane (TMS) as a standard substance

[Preparation of Base Composition]

A 200 mL round-bottom flask equipped with a magnetic stirrer was charged with 4.25 g of cesium carbonate ($Cs_2CO_3$, available from Fujifilm Wako Pure Chemical Corporation), 0.3 g of metallic sodium (available from Fujifilm Wako Pure Chemical Corporation) and 3.2 g of magnesium oxide (MgO, available from Fujifilm Wako Pure Chemical Corporation) under a nitrogen atmosphere. The round-bottom flask was placed on an aluminum block heater stirrer and heated and stirred for 1 hour at 250° C., after which the flask was removed from the aluminum block heater stirrer. The round-bottom flask was cooled to room temperature by air cooling, and a base composition was obtained.

[Synthesis of Amino Group-Containing Alkyl Substituted Aromatic Compound]

Example 1

A magnetic stirrer bar, 1.16 g of the base composition prepared in the above [Preparation of Base Composition], 0.80 g of MXDA, and 5.57 g of tetrahydrofuran (available from Fujifilm Wako Pure Chemical Corporation, super dehydrated, stabilizer-free grade) were inserted into a 30 mL autoclave under a nitrogen atmosphere, after which the autoclave was connected to an ethylene gas cylinder, and while ethylene gas (available from Japan Fine Products Corporation, ethylene purity: more than 99.9 vol. %) was blown in at a pressure of 0.99 MPa, the contents were stirred at 700 rpm and a temperature of 20 to 22.5° C. for 24 hours. After 24 hours, the gas supply from the ethylene cylinder and stirring were temporarily stopped to add 1.16 g of the base composition. After addition of the base composition, the ethylene supply and stirring were once again initiated, and the reaction was carried out for an additional 24 hours. The reaction was stopped by adding 4 mL of isopropyl alcohol to the reaction solution, and the residue containing the base composition was removed by suction filtration.

A separation operation was performed by adding a 1M aqueous HCl solution and dichloromethane to the filtrate, and the aqueous phase was collected. Next, a 1 M aqueous sodium hydroxide solution and dichloromethane were added, and the mixture was again subjected to a separation operation, after which the organic phase was collected. Dichloromethane was distilled off from the organic phase under reduced pressure, and thereby a mixture containing an amino group-containing alkyl substituted aromatic compound was obtained.

Liquid chromatography was then used to fractionate, from the mixture, α,α,α',α'-tetraethyl-meta-xylylenediamine represented by Formula (3) below and α,α,α'-triethyl-meta-xylylenediamine represented by Formula (4) below.

[Chem. 40]

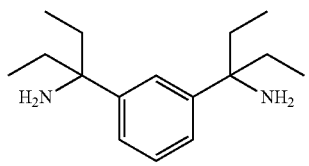

(3)

The various spectral data for the α,α,α',α'-tetraethyl-meta-xylylenediamine (3) were as follows.

$^1$H NMR (CDCl$_3$, tetramethylsilane) δ (ppm): 0.689, 0.704, 0.719 (12H, t, hydrogen of CH$_3$ in Ar—C(NH$_2$)—CH$_2$—CH$_3$), 1.639 to 1.711 (4H, m, hydrogen of CH$_2$ in Ar—C(NH$_2$)—CH$_2$—CH$_3$), 1.817 to 1.890 (4H, m, hydrogen of CH$_2$ in Ar—C(NH$_2$)—CH$_2$—CH$_3$), 7.214 to 7.235 (2H, Ar), 7.267 to 7.298 (1H, Ar), and 7.396 to 7.403 (1H, Ar).

$^{13}$C NMR (CDCl$_3$, tetramethylsilane) δ (ppm): 8.1 (x2), 36.2 (x2), 58.2, 123.4, 123.5, 127.6, and 146.1.

TOFMS analysis: 249.2285 as a theoretical value of m/e (C$_{16}$H$_{28}$N$_2$+H)$^+$, measured value of 249.231.

[Chem. 41]

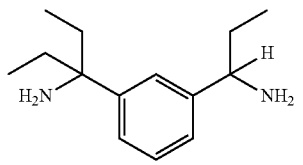

(4)

The various spectral data for the α,α,α'-triethyl-meta-xylylenediamine (4) were as follows.

$^1$H NMR (CDCl$_3$, tetramethylsilane) δ (ppm): 0.702, 0.717, 0.732 (6H, t, hydrogen of CH$_3$ in Ar—C(NH$_2$)—CH$_2$—CH$_3$), 0.837, 0.851, 0.866 (3H, t, hydrogen of CH$_3$ in Ar—CH(NH$_2$)—CH$_2$—CH$_3$), 1.623 to 1.751 (4H, m, hydrogen of CH$_2$ in Ar—C(NH$_2$)—CH$_2$—CH$_3$); 1.808 to 1.882 (2H, m, hydrogen of CH$_2$ in Ar—CH(NH$_2$)—CH$_2$—CH$_3$), 3.792, 3.806, 3.820 (1H, t, hydrogen of CH in Ar—CH(NH$_2$)—CH$_2$—CH$_3$), 7.140, 7.143, 7.146, 7.154, 7.157, 7.160 (1H, Ar), 7.244 to 7.301 (2H, Ar), and 7.313 to 7.320 (1H, Ar).

$^{13}$C NMR (CDCl$_3$, tetramethylsilane) δ (ppm): 8.1 (x2), 11.0, 32.6, 36.1 (x2), 58.0, 58.2, 123.7, 124.1, 124.5, 128.0, 146.0, and 146.8.

TOFMS analysis: 221.20123 as a theoretical value of m/e (C$_{14}$H$_{25}$N$_2$+H)$^+$, measured value of 221.199.

A mixture containing the amino group-containing alkyl substituted aromatic compound was subjected to GC analysis. From the results of the GC analysis, a peak stemming from α,α,α',α'-tetraethyl-meta-xylylenediamine (3) at a retention time of 19.6 minutes, and a peak stemming from α,α,α'-triethyl-meta-xylylenediamine (4) at a retention time of 18.3 minutes were observed, and the yields were 38% and 37%, respectively.

Example 2

A magnetic stirrer bar, 1.16 g of the base composition prepared in the above [Preparation of Base Composition], and 0.80 g of MXDA were inserted into a 30 mL autoclave under a nitrogen atmosphere, after which the autoclave was connected to an ethylene gas cylinder, and while ethylene gas (available from Japan Fine Products Corporation, ethylene purity: more than 99.9 vol. %) was blown in at a pressure of 0.99 MPa, the contents were stirred at 20 to 22° C. and 700 rpm for 24 hours. The reaction was stopped by adding 4 mL of isopropyl alcohol to the reaction solution. After the reaction stopped, 1 mL of the solution was removed, and residue containing the base composition was removed using a syringe filter (hole diameter of 0.45 μm, made of PTFE), and was subjected to GC analysis. From the results of the GC analysis, the yield of α,α,α',α'-tetraethyl-meta-xylylenediamine (3) was 2%, and the yield of α,α,α'-triethyl-meta-xylylenediamine (4) was 34%.

[Compound Properties]
<Handling Property>

10 mg of α,α,α',α'-tetraethyl-meta-xylylenediamine fractionated by liquid chromatography was weighed into an aluminum pan having a diameter of φ6 mm and a depth of 4 mm, and then left to stand in a nitrogen atmosphere at 25° C., 10° C., 0° C., −10° C., and −25° C. for 20 minutes at each temperature, and the material was evaluated visually and by touch to determine whether it was a liquid.

Similar evaluations were conducted using α,α,α'-triethyl-meta-xylylenediamine fractionated by liquid chromatography and meta-xylylenediamine (available from Tokyo Chemical Industry Co., Ltd.) in place of the α,α,α',α'-tetraethyl-meta-xylylenediamine.

The results are shown in Table 1. In the table, o indicates that the material was a liquid, and x indicates that the material was a solid. The fact that the compound is a liquid in a wide temperature range of 10° C. or lower means that heating is not necessary when weighing, mixing, and using the compound, and thus the compound is useful from the perspective of workability and energy savings.

<Storage Stability>

6 mg of α,α,α',α'-tetraethyl-meta-xylylenediamine fractionated by liquid chromatography was weighed into an aluminum pan having a diameter of φ6 mm and a depth of 4 mm, and then left to stand in air at 25° C., and the material was visually observed to determine the occurrence of a change to a white solid originating from carbonate. The α,α,α',α'-tetraethyl-meta-xylylenediamine was a transparent liquid even after left standing for 168 hours, and a conversion to a white solid due to the formation of a carbonate was not observed.

Similar evaluations were conducted with the exception that α,α,α'-triethyl-meta-xylylenediamine fractionated by liquid chromatography and meta-xylylenediamine were used in place of the α,α,α',α'-tetraethyl-meta-xylylenediamine. The α,α,α'-triethyl-meta-xylylenediamine was a transparent liquid even after left standing for 168 hours, and a conversion to a white solid due to the formation of a carbonate was not observed. The meta-xylylenediamine changed to a white solid when 30 minutes had passed.

The results are shown in Table 1. When the amino compound reacts with carbon dioxide to form a carbonate, the carbonate leads to a change in the raw material charging ratio due to a decrease in purity and to a decline in physical properties of the cured product when used as an epoxy resin curing agent. However, if a carbonate is not easily formed, the compound can be stored in air without performing special treatments such as adopting an inert gas atmosphere, providing a step of removing carbon dioxide gas by heat treatment, and pre-mixing the resin.

TABLE 1

| Compound | | α,α,α',α'-tetraethyl-meta-xylylenediamine | α,α,α'-triethyl-meta-xylylenediamine | meta-xylylenediamine |
|---|---|---|---|---|
| Handleability (liquid: o, solid: x) | 25° C. | o | o | o |
| | 10° C. | o | o | x |
| | 0° C. | o | o | x |
| | −10° C. | o | o | x |
| | −25° C. | o | o | x |
| Storage Stability | Time [h] to observation of white solid formation | >168 (not observed) | >168 (not observed) | 0.5 |

[Curing of Epoxy Resin]

Example 3

46.2 mg of α,α,α',α'-tetraethyl-meta-xylylenediamine fractionated by liquid chromatography was blended with 138.4 mg of "jER 828" (epoxy equivalent: 186 g/equivalent, solid content concentration: 100 mass %, liquid) available from Mitsubishi Chemical Corporation, and stirred, and an epoxy resin composition was obtained. Epoxy equivalent: The active hydrogen equivalent of the amine was adjusted to 1:1. The obtained epoxy resin composition was heated at a temperature increase of 5° C./minute to 250° C. and held at that temperature for 5 minutes, and as a result, a curing reaction proceeded, and an epoxy resin cured product was obtained. Differential scanning calorimetry (DSC) was performed, and the results indicated that the glass transition temperature was 50° C.

Note that the glass transition temperature of the epoxy resin cured product was determined through differential scanning calorimetry from 30 to 250° C. at a temperature increase rate of 5° C./minute using the "DCSC6220" differential scanning calorimeter (available from Seiko Instruments Inc.).

Example 4

18.7 mg of α,α,α'-triethyl-meta-xylylenediamine fractionated by liquid chromatography was blended with 63.1 mg of "jER 828" (epoxy equivalent: 186 g/equivalent, solid content concentration: 100 mass %, liquid) available from Mitsubishi Chemical Corporation, and stirred, and an epoxy resin composition was obtained. Epoxy equivalent: The active hydrogen equivalent of the amine was adjusted to 1:1. The obtained epoxy resin composition was heated at a temperature increase of 5° C./minute to 250° C. and held at that temperature for 5 minutes, and as a result, a curing reaction proceeded, and an epoxy resin cured product was obtained. Differential scanning calorimetry (DSC) was performed, and the results indicated that the glass transition temperature was 104° C.

[Synthesis of Amino Group-Containing Alkyl Substituted Aromatic Compound with Modified Ethylene Filling Conditions]

Example 5

A magnetic stirrer bar, 1.16 g of the base composition prepared in the above [Preparation of Base Composition], 0.80 g of MXDA (available from available from Tokyo Chemical Industry Co., Ltd.), and 5.57 g of tetrahydrofuran (available from Fujifilm Wako Pure Chemical Corporation, super dehydrated, stabilizer-free grade) were inserted into a 30 mL autoclave under an argon atmosphere. The autoclave was then placed in a 1° C. water bath and stirred at 700 rpm for 15 minutes to bring the reaction solution temperature to 3° C. While stirring was continued in the water bath, the autoclave was connected to an ethylene gas cylinder, and filled with ethylene gas (available from Japan Fine Products Corporation, ethylene purity: more than 99.9 vol. %) to a pressure of 2.0 MPa. The temperature of the water bath was changed to 20° C., and the reaction was carried out at 700 rpm for 24 hours. The reaction was stopped by adding 4 mL of isopropyl alcohol to the reaction solution, and the base composition was removed using a syringe filter (hole diameter of 0.45 μm, made of PTFE), and was subjected to gas chromatography analysis. The results are shown in Table 2.

Example 6

A magnetic stirrer bar, 1.16 g of the base composition prepared in the above [Preparation of Base Composition], 0.80 g of MXDA, and 5.57 g of tetrahydrofuran were inserted into a 30 mL autoclave under an argon atmosphere. The autoclave was then placed in a 1° C. water bath and stirred at 700 rpm for 15 minutes to bring the reaction solution temperature to 3° C. While stirring was continued in the water bath, the autoclave was connected to an ethylene gas cylinder and filled with ethylene gas to a pressure of 2.0 MPa. The temperature of the water bath was changed to 20° C., and stirring was performed at 700 rpm for 24 hours. After 24 hours, the stirring was temporarily stopped, and 1.16 g of the base composition was added. After addition of the base composition, the autoclave was inserted once again into the 1° C. water bath and stirred at 700 rpm for 15 minutes, the reaction temperature was set to 3° C., and the autoclave was filled with ethylene gas to a pressure of 2.0 MPa while stirring in the water bath was continued. The reaction was carried out for 24 hours after the filling with ethylene gas. The reaction was stopped by adding 4 mL of isopropyl alcohol to the reaction solution, and the base composition was removed using a syringe filter (hole diameter of 0.45 μm, made of PTFE), and was subjected to gas chromatography analysis. The results are shown in Table 2.

Example 7

A magnetic stirrer bar, 1.16 g of the base composition prepared in the above [Preparation of Base Composition], 0.80 g of MXDA (available from available from Tokyo Chemical Industry Co., Ltd.), and 5.57 g of tetrahydrofuran (available from Fujifilm Wako Pure Chemical Corporation, super dehydrated, stabilizer-free grade) were inserted into a 30 mL autoclave under an argon atmosphere. The autoclave was placed in a water bath at 20° C. and stirred at 700 rpm, the reaction solution temperature was adjusted to 20° C., and the autoclave was connected to an ethylene gas cylinder and filled with ethylene gas (available from Japan Fine Products Corporation, ethylene purity: more than 99.9 vol. %) to a pressure of 2.0 MPa. The reaction was carried out at 700 rpm for 24 hours after the ethylene filling. The reaction was stopped by adding 4 mL of isopropyl alcohol to the reaction solution, and the base composition was removed using a syringe filter (hole diameter of 0.45 μm, made of PTFE), and was subjected to gas chromatography analysis. The results are shown in Table 2.

Example 8

A magnetic stirrer bar, 1.16 g of the base composition prepared in the above [Preparation of Base Composition], 0.80 g of MXDA (available from available from Tokyo Chemical Industry Co., Ltd.), and 5.57 g of tetrahydrofuran (available from Fujifilm Wako Pure Chemical Corporation, super dehydrated, stabilizer-free grade) were inserted into a 30 mL autoclave under an argon atmosphere. The autoclave was then placed in a 1° C. water bath and stirred at 700 rpm for 15 minutes to bring the reaction solution temperature to 3° C. While stirring was continued in the water bath, the autoclave was connected to an ethylene gas cylinder, and the autoclave was filled with ethylene gas (available from Japan Fine Products Corporation, ethylene purity: more than 99.9 vol. %) to a pressure of 0.99 MPa. The temperature of the water bath was changed to 20° C., and the reaction was carried out at 700 rpm for 24 hours. The reaction was stopped by adding 4 mL of isopropyl alcohol to the reaction solution, and the base composition was removed using a syringe filter (hole diameter of 0.45 μm, made of PTFE), and was subjected to gas chromatography analysis. The results are shown in Table 2.

TABLE 2

| | Example 5 | Example 6 | Example 7 | Example 8 |
|---|---|---|---|---|
| Reaction solution temperature [° C.] when filled with ethylene | 3 | 3 | 20 | 3 |
| Ethylene filling pressure [MPa] | 2.0 | 2.0 | 2.0 | 0.99 |
| Ethylene trimolecular adduct yield [%] | 69 | 2 | 44 | 38 |
| Ethylene tetramolecular adduct yield [%] | 12 | 80 | 2 | 2 |

Note that the structure of the ethylene trimolecular adduct obtained in Examples 5 to 8 was the compound represented by Formula (4) (α,α,α'-triethyl-meta-xylylenediamine).

The various spectral data for the α,α,α'-triethyl-meta-xylylenediamine were as follows.

$^1$H NMR (CDCl$_3$, tetramethylsilane) δ (ppm): 0.702, 0.717, 0.732 (6H, t, hydrogen of CH$_3$ in Ar—C(NH$_2$)—CH$_2$—CH$_3$), 0.837, 0.851, 0.866 (3H, t, hydrogen of CH$_3$ in Ar—CH(NH$_2$)—CH$_2$—CH$_3$), 1.623 to 1.751 (4H, m, hydrogen of CH$_2$ in Ar—C(NH$_2$)—CH$_2$—CH$_3$); 1.808 to 1.882 (2H, m, hydrogen of CH$_2$ in Ar—CH(NH$_2$)—CH$_2$—CH$_3$), 3.792, 3.806, 3.820 (1H, t, hydrogen of CH in Ar—CH(NH$_2$)—CH$_2$—CH$_3$), 7.140, 7.143, 7.146, 7.154, 7.157, 7.160 (1H, Ar), 7.244 to 7.301 (2H, Ar), and 7.313 to 7.320 (1H, Ar).

$^{13}$C NMR (CDCl$_3$, tetramethylsilane) δ (ppm): 8.1 (x2), 11.0, 32.6, 36.1 (x2), 58.0, 58.2, 123.7, 124.1, 124.5, 128.0, 146.0, and 146.8.

TOFMS analysis: 221.20123 as a theoretical value of m/e (C$_{14}$H$_{25}$N$_2$+H)$^+$, measured value of 221.199.

Note that the structure of the ethylene tetramolecular adduct obtained in Examples 5 to 8 was the compound represented by Formula (3) (α,α,α',α'-tetraethyl-meta-xylylenediamine).

The various spectral data for the α,α,α',α'-tetraethyl-meta-xylylenediamine were as follows.

$^1$H NMR (CDCl$_3$, tetramethylsilane) δ (ppm): 0.689, 0.704, 0.719 (12H, t, hydrogen of CH$_3$ in Ar—C(NH$_2$)—CH$_2$—CH$_3$), 1.639 to 1.711 (4H, m, hydrogen of CH$_2$ in Ar—C(NH$_2$)—CH$_2$—CH$_3$), 1.817 to 1.890 (4H, m, hydrogen of CH$_2$ in Ar—C(NH$_2$)—CH$_2$—CH$_3$), 7.214 to 7.235 (2H, Ar), 7.267 to 7.298 (1H, Ar), and 7.396 to 7.403 (1H, Ar).

$^{13}$C NMR (CDCl$_3$, tetramethylsilane) δ (ppm): 8.1 (x2), 36.2 (x2), 58.2, 123.4, 123.5, 127.6, and 146.1.

TOFMS analysis: 249.2285 as a theoretical value of m/e (C$_{16}$H$_{28}$N$_2$+H)$^+$, measured value of 249.231.

As is clear from the above results, when the temperature of the reaction solution at the time of ethylene filling was from 0 to 10° C. and the ethylene filling pressure was from 1.5 to 2.3 MPa, compounds in which ethylene was added at a higher ratio such as an ethylene trimolecular adduct and an ethylene tetramolecular adduct were obtained (Examples 5 and 6). In particular, when the base composition was divided into two or more portions and then added (Example 6), the ethylene tetramolecular adduct was obtained at an even higher ratio.

INDUSTRIAL APPLICABILITY

According to the present invention, an amino group-containing alkyl substituted aromatic compound that is useful as an intermediate raw material or such of a compound can be provided, and thus the present invention is industrially applicable in fields such as resins and other industrial products, pharmaceuticals, and fragrances.

The invention claimed is:

1. A method for producing a compound represented by Formula (1-1), the method comprising subjecting a compound represented by Formula (5-1) to an addition reaction to add ethylene and/or propylene in the presence of a base:

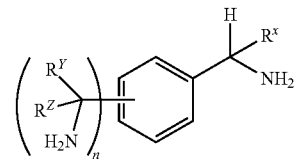

(5-1)

where in Formula (5-1), $R^X$ to $R^Z$ each independently represent a hydrogen atom, an ethyl group, an n-propyl group, or an isopropyl group, and n is an integer of from 1 to 3;

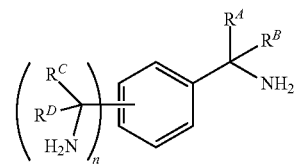

(1-1)

where in Formula (1-1), $R^A$ to $R^D$ each independently represent a hydrogen atom, an ethyl group, an n-propyl group, or an isopropyl group, and n is an integer of from 1 to 3, wherein at least two of $R^A$ to $R^D$ are independently an ethyl group, an n-propyl group, or an isopropyl group, and Formula (1-1) excludes:

a case where n is 1, a —C($R^C$)($R^D$)(NH$_2$) group is at para position or at meta position, either $R^A$ or $R^B$ and either $R^C$ or $R^D$ are each an n-propyl group, and the remaining two of $R^A$ to $R^D$ are hydrogen atoms; and a case where n is 1, a —$C(R^C)(R^D)(NH_2)$ group is at ortho position, either $R^A$ or $R^B$ and either $R^C$ or $R^D$ are each an ethyl group, and the remaining two of $R^A$ to $R^D$ are hydrogen atoms.

2. A method for producing a compound represented by Formula (1-2), the method comprising contacting a compound represented by Formula (5-2) with ethylene and subjecting the compound to alkylation in the presence of a base, wherein a temperature of a reaction solution at the time of ethylene filling is from 0 to 10° C., and a filling pressure of the ethylene is from 1.5 to 2.3 MPa:

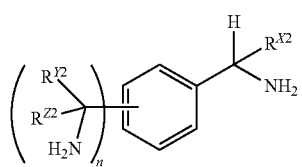

(5-2)

where in Formula (5-2), $R^{X2}$ to $R^{Z2}$ each independently represent a hydrogen atom or an ethyl group, and n is an integer of from 1 to 3;

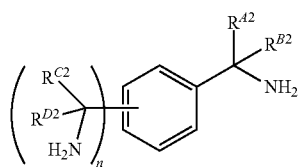

(1-2)

where in Formula (1-2), $R^{A2}$ to $R^{D2}$ each independently represent a hydrogen atom or an ethyl group, and n is an integer of from 1 to 3, wherein at least two of $R^{A2}$ to $R^{D2}$ are ethyl groups.

3. The compound production method according to claim 1, wherein the base is a base composition comprising:

at least one alkali metal-containing compound (A) which is selected from the group consisting of rubidium carbonate, rubidium hydroxide, cesium carbonate, and cesium hydroxide; and a metallic sodium (B).

4. The compound production method according to claim 1, comprising dividing the base into two or more portions and introducing into a reaction system.

5. The compound production method according to claim 1, wherein n in Formula (5-1) is 1.

6. The compound production method according to claim 1, wherein the compound represented by Formula (5-1) comprises at least one compound selected from the group consisting of o-xylylenediamine, m-xylylenediamine, p-xylylenediamine, 1,2,3-benzene trimethanamine, 1,2,4-benzene trimethanamine and 1,2,4,5-benzene tetramethanamine.

7. The compound production method according to claim 1, wherein the compound represented by Formula (5-1) comprises m-xylylenediamine.

8. The compound production method according to claim 1, wherein the compound represented by Formula (1-1) is represented by Formula (2-1):

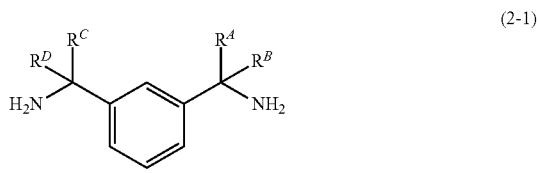

(2-1)

where in Formula (2-1), at least two of $R^A$ to $R^D$ are the same group selected from the group consisting of an ethyl group, an n-propyl group, and an isopropyl group, and the remainder of $R^A$ to $R^D$ is a hydrogen atom, wherein, when two of $R^A$ to $R^D$ are n-propyl groups, Formula (2-1) excludes a case where either $R^A$ or $R^B$, and either $R^C$ or $R^D$ are each an n-propyl group;

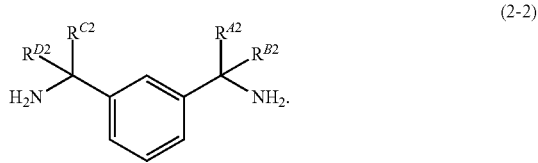

(2-2)

9. The compound production method according to claim 1, wherein at least three of $R^A$ to $R^D$ in Formula (1-1) are ethyl groups, and the remainder of $R^A$ to $R^D$ is a hydrogen atom.

10. The compound production method according to claim 1, wherein the compound represented by Formula (1-1) is represented by Formula (3) or Formula (4):

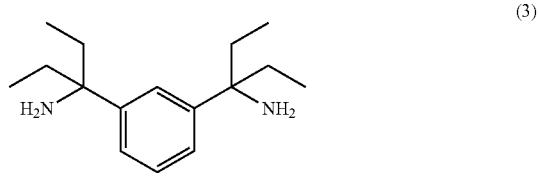 [SMILES: CCC(N)(CC)c1cccc(C(N)(CC)CC)c1]

(3)

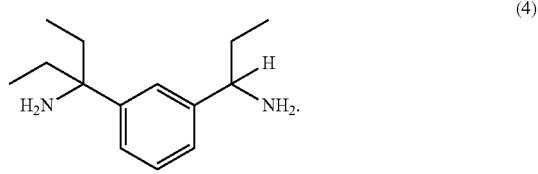 [SMILES: CCC(N)c1cccc(C(N)(CC)CC)c1]

(4)

11. A compound represented by Formula (1-1):

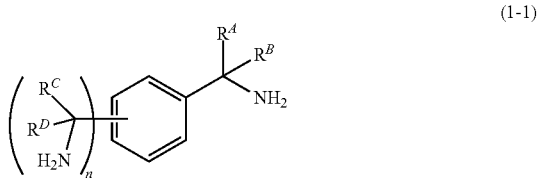

(1-1)

where in Formula (1-1), $R^A$ to $R^D$ each independently represent a hydrogen atom, an ethyl group, an n-propyl group, or an isopropyl group, and n is an integer of from 1 to 3, wherein at least two of $R^A$ to $R^D$ are independently an ethyl group, an n-propyl group, or an isopropyl group, and Formula (1-1) excludes:

a case where n is 1, a —C(R$^C$)(R$^D$)(NH$_2$) group is at para position or at meta position, either R$^A$ or R$^B$ and either R$^C$ or R$^D$ are each an n-propyl group, and the remaining two of R$^A$ to R$^D$ are hydrogen atoms; and a case in where n is 1, a —C(R$^C$)(R$^D$)(NH$_2$) group is at ortho position, either R$^A$ or R$^B$ and either R$^C$ or R$^D$ are each an ethyl group, and the remaining two of R$^A$ to R$^D$ are hydrogen atoms.

12. The compound according to claim 11, wherein n in Formula (1-1) is 1.

13. The compound according to claim 11, represented by Formula (2-1):

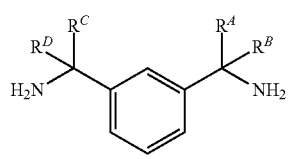
(2-1)

where in Formula (2-1), at least two of R$^A$ to R$^D$ are the same group selected from the group consisting of an ethyl group, an n-propyl group, and an isopropyl group, and the remainder of R$^A$ to R$^D$ is a hydrogen atom, wherein, when two of R$^A$ to R$^D$ are n-propyl groups, Formula (2-1) excludes a case where either R$^A$ or R$^B$, and either R$^C$ or R$^D$ are each an n-propyl group.

14. The compound according to claim 11, represented by Formula (3)

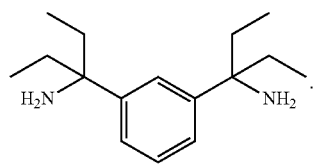
(3)

15. The compound according to claim 11, represented by Formula (4)

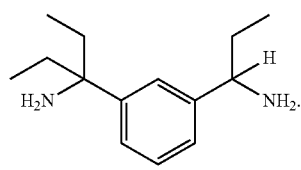
(4)

16. A method for producing an amine composition containing a compound represented by Formula (1-2), the method comprising contacting a compound represented by Formula (5-2) with ethylene and subjecting the compound to alkylation in the presence of a base, wherein a temperature of a reaction solution at the time of the ethylene filling is from 0 to 10° C., and a filling pressure of the ethylene is from 1.5 to 2.3 MPa:

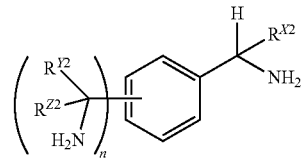
(5-2)

where in Formula (5-2), R$^{X2}$ to R$^{Z2}$ each independently represent a hydrogen atom or an ethyl group, and n is an integer of from 1 to 3;

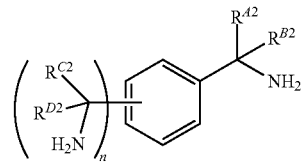
(1-2)

where in Formula (1-2), R$^{A2}$ to R$^{D2}$ each independently represent a hydrogen atom or an ethyl group, and n is an integer of from 1 to 3, wherein at least two of R$^{A2}$ to R$^{D2}$ are ethyl groups.

17. The compound production method according to claim 2, wherein the base is a base composition comprising:

at least one alkali metal-containing compound (A) which is selected from the group consisting of rubidium carbonate, rubidium hydroxide, cesium carbonate, and cesium hydroxide; and a metallic sodium (B).

18. The compound production method according to claim 2, comprising dividing the base into two or more portions and introducing into a reaction system.

19. The compound production method according to claim 2, wherein n in Formula (5-2) is 1.

20. The compound production method according to of claim 2, wherein the compound represented by Formula (1-2) is represented by Formula (2-2):

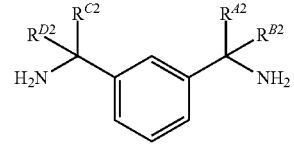
(2-2)

where in Formula (2-2), at least two of R$^{A2}$ to R$^{D2}$ are ethyl groups, and the remainder of R$^{A2}$ to R$^{D2}$ is a hydrogen atom.

21. The compound production method according to claim 2, wherein at least three of R$^{A2}$ to R$^{D2}$ in Formula (1-2) are ethyl groups, and the remainder of R$^{A2}$ to R$^{D2}$ is a hydrogen atom.

22. The compound production method according to claim 2, wherein the compound represented by Formula (5-2) comprises at least one compound selected from the group consisting of o-xylylenediamine, m-xylylenediamine, p-xylylenediamine, 1,2,3-benzene trimethanamine, 1,2,4-benzene trimethanamine and 1,2,4,5-benzene tetramethanamine.

* * * * *